(12) United States Patent
McDonald et al.

(10) Patent No.: US 9,108,858 B2
(45) Date of Patent: *Aug. 18, 2015

(54) NANOFILAMENTS OF CATALYTIC MATERIALS FOR CHEMICAL PROCESS IMPROVEMENTS

(71) Applicant: Louisiana Tech University Research Foundation; a Division of Louisiana Tech University Foundation, Inc., Ruston, LA (US)

(72) Inventors: John McDonald, West Monroe, LA (US); Chester Wilson, Ruston, LA (US); Joshua Brown, West Monroe, LA (US)

(73) Assignee: Louisiana Tech University Research Foundation; a Division of Louisiana Tech University Foundation, Ruston, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/546,170

(22) Filed: Nov. 18, 2014

(65) Prior Publication Data

US 2015/0071843 A1   Mar. 12, 2015

Related U.S. Application Data

(63) Continuation of application No. 14/151,560, filed on Jan. 9, 2014, now Pat. No. 8,895,631, which is a continuation of application No. 13/722,613, filed on Dec. 20, 2012, now Pat. No. 8,629,189, which is a continuation-in-part of application No. 12/726,106, filed on Mar. 17, 2010, now Pat. No. 8,399,527.

(60) Provisional application No. 61/160,949, filed on Mar. 17, 2009.

(51) Int. Cl.

| | | |
|---|---|---|
| *C01C 1/04* | (2006.01) |
| *B01J 12/00* | (2006.01) |
| *B01J 19/00* | (2006.01) |
| *B01J 19/24* | (2006.01) |
| *C10G 2/00* | (2006.01) |
| *C25D 5/18* | (2006.01) |
| *C25D 11/04* | (2006.01) |
| *C25D 11/20* | (2006.01) |
| *B01J 37/34* | (2006.01) |
| *B01J 23/46* | (2006.01) |
| *B01J 23/745* | (2006.01) |
| *B01J 23/75* | (2006.01) |
| *B01J 35/00* | (2006.01) |
| *C07C 1/04* | (2006.01) |
| *H01M 10/052* | (2010.01) |
| *H01M 12/08* | (2006.01) |
| *C25D 3/12* | (2006.01) |
| *C25D 11/08* | (2006.01) |
| *C25D 11/12* | (2006.01) |
| *C25D 5/00* | (2006.01) |

(52) U.S. Cl.
CPC ............ *C01C 1/0411* (2013.01); *B01J 12/007* (2013.01); *B01J 19/006* (2013.01); *B01J 19/24* (2013.01); *B01J 19/249* (2013.01); *B01J 23/462* (2013.01); *B01J 23/745* (2013.01); *B01J 23/75* (2013.01); *B01J 35/006* (2013.01); *B01J 37/341* (2013.01); *B01J 37/348* (2013.01); *C07C 1/0455* (2013.01); *C10G 2/33* (2013.01); *C10G 2/332* (2013.01); *C25D 5/18* (2013.01); *C25D 11/045* (2013.01); *C25D 11/20* (2013.01); *B01J 2219/0009* (2013.01); *B01J 2219/00063* (2013.01); *B01J 2219/00162* (2013.01); *B01J 2219/00777* (2013.01); *B01J 2219/248* (2013.01); *B01J 2219/2479* (2013.01); *C25D 3/12* (2013.01); *C25D 5/006* (2013.01); *C25D 11/08* (2013.01); *C25D 11/12* (2013.01); *H01M 10/052* (2013.01); *H01M 12/08* (2013.01)

(58) Field of Classification Search
CPC ........ B01J 19/24; B01J 23/462; B01J 23/745; B01J 23/75; B01J 2219/2479; B01J 2219/248; C10G 2/332; C10G 2/33; C07C 10/455
USPC .......................................................... 423/362
See application file for complete search history.

(56) References Cited

U.S. PATENT DOCUMENTS

2009/0117014 A1 *   5/2009   Carpenter ..................... 422/148

* cited by examiner

*Primary Examiner* — Jafar Parsa
(74) *Attorney, Agent, or Firm* — Jones Walker LLP

(57) ABSTRACT

A Haber-Bosch process including the steps of providing a reactor having a substrate with catalyst filaments formed thereon. The catalyst filaments are formed of a metal including iron. A nitrogen compound and hydrogen are injected into the reactor such that at least a portion of the nitrogen compound and hydrogen contact the catalyst filaments. The nitrogen compound and hydrogen are reacted with the catalyst filaments at a temperature of less than about 600° F. and a pressure of less than about 2000 psig.

10 Claims, 13 Drawing Sheets

NANOFILAMENTS OF CATALYTIC MATERIALS FOR CHEMICAL PROCESS IMPROVEMENTS

CROSS REFERENCE TO RELATED APPLICATIONS

This application is a continuation of U.S. application Ser. No. 14/151,560 filed on Jan. 9, 2014, which application was a continuation of U.S. application Ser. No. 13/722,613 filed on Dec. 20, 2012, which application was a continuation-in-part of U.S. application Ser. No. 12/726,106, filed on Mar. 17, 2010, which claims the benefit under 35 USC §119(e) of U.S. provisional application Ser. No. 61/160,949 filed Mar. 17, 2009, all of which this application claims priority to and which are incorporated by reference herein in their entirety.

FIELD AND BACKGROUND OF INVENTION

The present invention generally relates to catalytic processes and in particular embodiments, catalyst shapes and structures to enhance catalytic activity.

Catalytic processes are used in enumerable chemical processes, with some estimates suggesting that 90% of all commercially produced chemical products involve catalysts at some stage of their manufacture. Examples include catalytic cracking in the petroleum refining industry, catalytic oxidation in many large-scale chemical production methods, highly specialized catalytic reactions in fine chemical production, catalytic hydrogenation in the food processing industry, polymer production, and reduction of pollutants in transportation and industrial emissions.

Several factors affect the efficiency of catalytic processes, including optimizing reactant exposure to the catalyst, activation energy of the catalyst, minimizing the catalyst's degradation, and improving the regeneration of catalyst when required. Improvements in one or more of these factors would be beneficial across a broad spectrum of catalytic processes.

DETAILED DESCRIPTION OF SELECTED EMBODIMENTS

Figure 1:
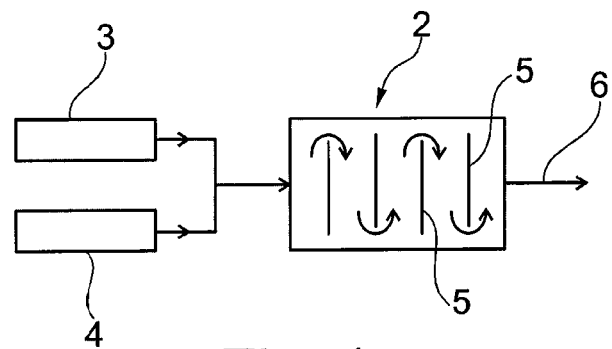
FIG. 1 schematically illustrates a very basic reactor system.
Figure 2:
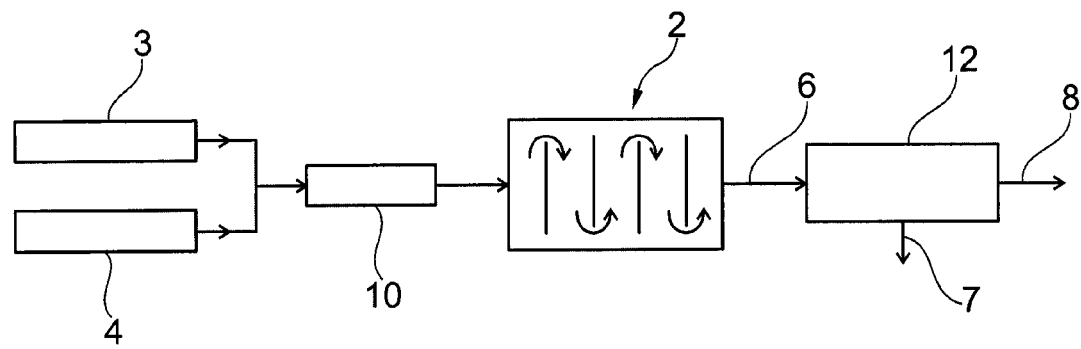
FIG. 2 schematically illustrates a slightly more complex reactor system.

One embodiment of the invention is a Fischer-Tropsch process (FTP) wherein a gaseous carbon compound and hydrogen are injected into a reactor such that at least a portion of the carbon compound and hydrogen contact a catalyst material and are reacted with the catalyst (often at above ambient pressure and temperature) in order to form hydrocarbon chains. As suggested in FIG. 1, such a process would include a reactor 2 which is fed from a carbon compound source 3 and a hydrogen source 4. Catalyst substrate elements 5 would be positioned in reactor 2 and have the catalyst formed thereon. The carbon compound and hydrogen will pass through the reactor 2 and react with the catalyst to produce a hydrocarbon output product 6. Many variations of this basic process are possible. For example, FIG. 2 illustrates a preheater 10 positioned before reactor 2 and a condenser 12 positioned thereafter. The preheater 10 would raise the temperature of the carbon compound and hydrogen from their initial temperatures to a temperature closer to that desired at the reactor input. Condenser 12 would operate to condense gaseous hydrocarbons, remove water 7 from the output product 6, and to provide a final de-watered liquid hydrocarbon product 8.

Figure 3A:
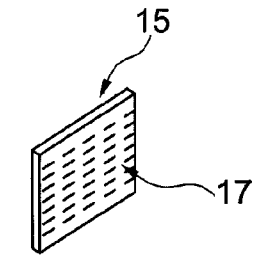
FIGS. 3A to 3D illustrate different substrates with catalyst formed thereon.
Figure 3B:
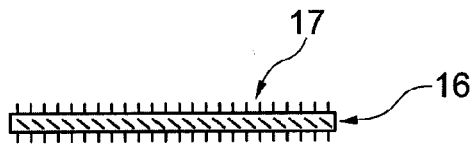

The carbon compound may take many different forms depending on the type of catalyst employed, the end product desired, and the particular process parameters. In many FTP systems, the carbon compound will typically be CO, but could be other carbon compounds. The hydrogen is typically in the form of molecular hydrogen ($H_2$), but could be other hydrogen containing compounds. The catalyst substrate elements 5 may take enumerable shapes or forms. FIG. 3A illustrates a flat plate structure 15 while FIG. 3B illustrates a rod structure 16 acting as a substrate. Other non-limiting examples of substrate shapes/structures include tubular substrates, either straight or curved (e.g., spiraled), and washer-shaped substrates. Typically, the substrates will be formed of metal or have a metal coating applied to the surface of the substrate onto which the catalyst is formed. Certain embodiments may include conductive metals such as aluminum, cobalt, iron, copper, platinum, palladium, rhodium, ruthenium, chromium, nickel, other noble metals, other transition metals, other conductive metals/alloys. Substrates may take irregular forms such as a comparatively planar surface which has a large number of micro-structures formed thereon. In one example, the micro-structures are a field of micro-needles (defined below) which then have a catalyst material sputtered on as a thin film. In certain embodiments, nominal dimensions for such substrate micro-structures may range from about 5 nanometers to about 1 micron.

Figure 3C:
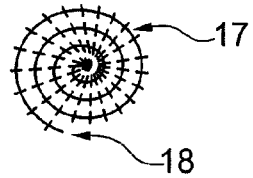
Figure 3D:
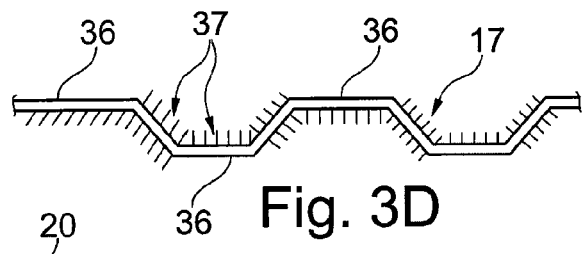

In one embodiment, the substrate is an aluminum foil type material 18 which is rolled to provide concentric layers of substrate material (see FIG. 3C) having catalyst micro-structures 17 formed thereon. In another embodiment (FIG. 3D), the substrate will be non-uniform with bearing surfaces 36 and protected recessed surfaces 37. The catalyst micro-structures 17 could be formed on the recessed surfaces 37 in a location protected from mechanical engagement with other surfaces while bearing surfaces 36 would contact the walls of the reactor or other catalyst substrate elements. In many embodiments, the substrate element is substantially nonporous, meaning that the substrate is sufficiently nonporous that under given reaction pressures and flow rates, the reactants will flow around and past the substrates (thus contacting microstructures on the substrate surface) rather than through the substrate material.

In certain embodiments, catalyst will be formed on the substrate as elongated micro-structures. One version of these micro-structures have a width of less than about 1 um and include a crystal structure having substantially no grain boundaries. In other versions, the micro-structures may also contain grain boundaries, either engineered and controlled for specific effects or simply allowed as inherent part of a particular manufacturing process. Although the size is greatly exaggerated, FIGS. 3A and 3B suggest how these elongated micro-structures 17 (or "micro-needles" 17) may be formed on a substrate. Although the width or diameter of micro-needles 17 in many embodiments will range anywhere from a few nanometers to about 1 um (or any sub-range therebetween), certain width ranges for micro-needles 17 include between about 10 nm and about 500 nm or between about 20 nm and about 100 nm. Micro-needles 17 are elongated in the sense that they will have a length at least five times their diameter, and more commonly a length at least 5 times to about 10,000 times their diameter (or any sub-range there between) or alternatively, about 10 um to about 5 millimeters in length (or any sub-range there between).

As used herein, a crystal structure having no grain boundaries means all crystals in the structure have a predominantly uniform orientation in a single crystalline plane. One example of how the orientation of the crystalline plane may be defined is the Miller Index. Thus, the crystalline plane may be defined as [100], [111], etc. Such a crystal structure has substantially no grain boundaries when the mis-orientation between grains is at a relatively low angle, for example less than approximately 10 to 15 degrees. In certain embodiments, the minimization of grain boundaries is accomplished by limiting the micro-needle diameter to about 100 nm or less.

In many embodiments, the micro-needles will be formed on the substrate or a relevant portion of the substrate (i.e., not necessarily the entire substrate surface) at a given pore density. Pore density is defined as the total area of micro-needles (i.e., the sum of cross-sectional area of the needles) attached to the substrate divided by the substrate surface area over which needles are distributed. In one embodiments, the pore density is approximately 50%, but in other embodiments the pore density could range from about 10% to about 90% (or any sub-range there between). Likewise, less common embodiments could exist with pore densities around the 1% to 5% range or the 90% to 100% range.

The catalyst materials employed will often depend on the type of FTP being utilized. In certain embodiments, the catalyst material will be at least one of cobalt, iron, nickel, or ruthenium. The micro-needles will often be formed completely of one element. Alternatively, the micro-needles could be a non-catalyst material coated with a catalyst layer. Other embodiments could include micro-needles formed from a first catalyst material (e.g., cobalt) and capped with a section of a second catalyst material (e.g., ruthenium). The catalyst materials could also be alloys whose compositions include cobalt, iron, or ruthenium together with other elements or compounds. Four particular embodiments for constructing catalyst structure could include: 1) simple electroplating of one metal as one crystal; 2) one metal in one or more crystal planes for a desired effect; 3) two or more metals all electroplated in successive layers with each successive layer essentially "capping" the previous layer and leaving all previous material exposed; and 4) deposition of another material on top of existing needles (or other structures) with the intention of completely covering the needle/structure. The deposition technique described in (4) could be by evaporation (thermal or electron beam), sputtering, reactive sputtering, self-assembled monolayers, multiple layers from a polyelectrolyte multi-layer technique, or chemical vapor deposition.

Figure 4A:
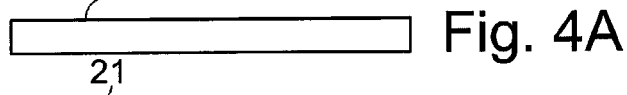
FIGS. 4A to 4D illustrate a series of steps used in one method of forming catalyst on a substrate.
Figure 4B:
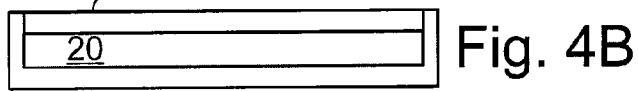
Figure 4C:
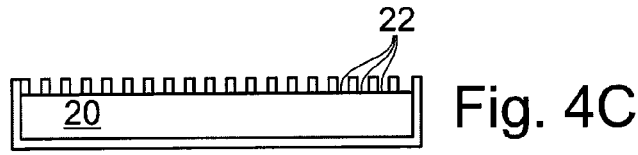

Numerous processes may be used to form the micro-needles described above onto a substrate. In one embodiment suggested in FIG. 4A to 4D, the substrate 20 (e.g., a plate seen from the side) may be a conductive material such as aluminum, copper, titanium, nickel, iron, chromium, tungsten or an alloy of these materials. A non-conductive layer 21 is formed or is allowed to form on the surface of the substrate 20 (FIG. 4B). For example, where the substrate 20 is aluminum, an aluminum oxide coating may be formed on substrate 20. In one embodiment, the aluminum oxide coating is formed through an anodization process. Prior to anodization, the substrate is typically cleaned in either a hot soak cleaner or in a solvent bath and may be etched in sodium or similar compounds. The anodized aluminum layer is grown by passing a direct current through an electrolytic solution (e.g., sulfuric acid), with the aluminum object serving as the anode. Example voltages may range from 1 to 300 V DC, although more typically fall in the range of 15 to 21 V. Example anodizing currents vary with the area of aluminum being anodized, but typically may range from 0.3 to 3 amperes of current per square decimeter (20 to 200 mA/in$^2$).

Anodizing may be performed in an acid solution which slowly dissolves the aluminum oxide. The acid action is balanced with the oxidation rate to form a coating with microscopic pores 22 suggested in FIG. 4C. Conditions such as electrolyte concentration, acidity, solution temperature, and current are controlled to allow the formation of a consistent oxide layer and may be used to control the size of the pores. Anodizing at lower temperatures tends to decrease the density of the pores; the pore and ultimately needle/micro-structure nominal diameter is decreased and the aluminum oxide mass is increased. Increased current tends to increase the diameter of the pores in the aluminum oxide and the resulting needle/structure density. As explained in more detail below, the pore size is configured to obtain the desired diameter of the micro-needles. The thickness of the anodized layer 21 may vary with one example being an approximately 50 um thick aluminum oxide coating.

Figure 4D:
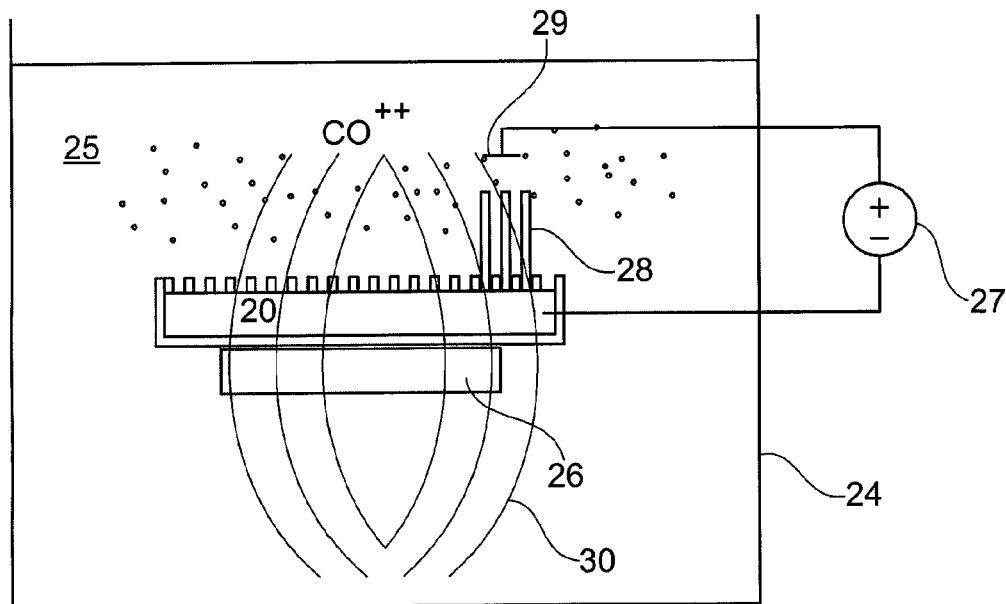

As suggested in FIG. 4D, one embodiment involves placing the substrate 20 having anodized layer 21 and micro-pores 22 in a solution containing catalyst ions. In the example of FIG. 4D, the catalyst ions are cobalt ions formed by dissolving CoNO$_3$ in an aqueous solution in a (molar) concentration range of about 0.05 to about 2.0. Alternatively the catalyst ions may be formed by dissolving CoSO$_4$ in an aqueous solution in a (molar) concentration range of about 0.05 to about 6.0. FIG. 4D illustrates the cathode of DC voltage source 27 being connected to substrate 20 and the anode 29 being positioned in the catalyst containing solution. As a voltage is applied between substrate 20 and anode 29, elongated cobalt structures (micro-needles 28) will grow in the pores 22. It will be understood that the size of the pores 22 will govern the diameter of the micro-needles 28. Factors affecting growth of the catalyst needles include temperature of the solution, strength of the electric field, solution chemistry, and spatial orientation of the electrodes (e.g., distance apart). Typically, the further the anode is from the substrate, the greater the tendency for the micro-needles to form in an elongated manner. In the embodiment of FIG. 4D, the electrolyte temperature may range between about 10° C. and about 50° C.; the current density may range between about 1 to 500 mA/cm2 with 50 mA/cm$^2$ being a typical value when electroplating in pulse-reverse mode; and the anode 29 is positioned at least about 2 cm to about 30 cm from the surface of the substrate 20. Of course, these are merely example parameters and those skilled in the art will recognize innumerable alternative parameters and techniques.

In other embodiments, sources of the Co or Fe ions might be Co(NO$_3$)$_2$, FeCl$_2$, and other similar compounds. In certain embodiments, the electric current may alternate or be pulsed. In an alternate embodiment, the micro-needles will be formed in the presence of a magnetic field in order to aid in the uniform orientation of the crystal lattice as the micro-needles are grown. As one example, a magnet 26 may be positioned below substrate 20 in order to create a magnetic field having an orientation suggested by magnetic flux lines 30. As an alternative to applying the magnetic field during micro-needle growth, the fully formed micro-needles could be subject to a magnetic field and heat treatment process to effect a desired dipole alignment. Nevertheless, it should be clear that the invention also includes micro-needles grown in the absence of any applied magnetic field.

While the above examples form the micro-structures through a electroplating technique, numerous other processes could be used to form the micro-structures, non-limiting examples of which include low pressure chemical vapor deposition (LPCVD), plasma enhanced chemical vapor deposition (PECVD), or sputtering.

Figure 5A:
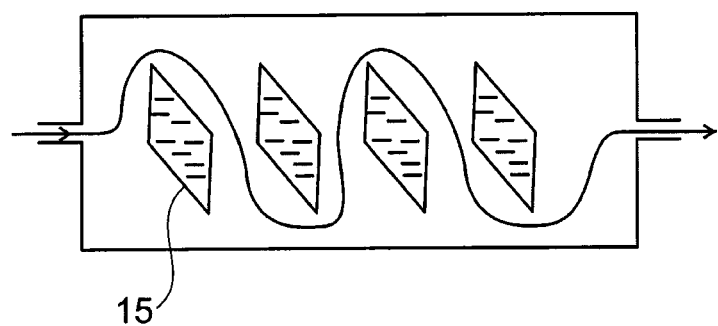
FIGS. 5A and 5B schematically illustrate the orientation of catalyst substrate elements in two different reactor arrangements.
Figure 5B:
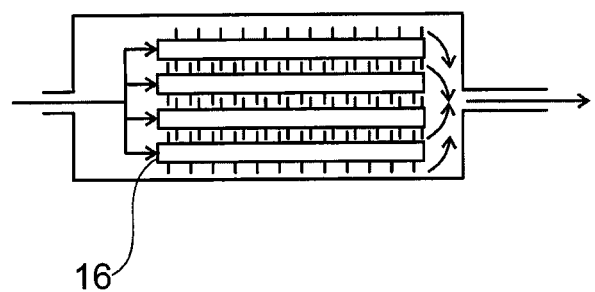

Once the catalyst micro-needles are formed on a substrate, one or more substrate elements having the micro-needles may be positioned within a reactor. While certain orientations of the substrate elements in the reactor may produce a more efficient reaction, the exact orientation of the substrate elements may vary significantly from embodiment to embodiment. As suggested by FIG. 5A, a plate substrate 15 could be oriented such that the surfaces with micro-needles 17 are perpendicular to the overall flow direction of the reactants. While hidden from view, these plate substrates 15 would have micro-needles formed on the front (shown in FIG. 5A) and back (view hidden in FIG. 5A) sides. Although spacing of plate substrates 15 is greatly exaggerated, FIG. 5A suggests how the plates could be positioned to direct flow around the plates to maximize contact with the catalyst micro-needles. Regarding rod substrates 16, these could be positioned with their long axis parallel to the overall flow direction of reactants as suggested by FIG. 5B. Likewise, the substrates seen in FIGS. 3C and 3D would be positioned with their long axes parallel to the overall direction of reactant flow.

The reactor parameters may differ considerably depending on variables such as the type of catalyst employed, the input reactants and the final product sought. As one nonlimiting example, where H$_2$ and CO are the reactants, cobalt micro-needles are positioned on rod substrates in the reactor, and the intended product is diesel type hydrocarbons (i.e., ranging from approximately C$_{10}$H$_{22}$ to C$_{25}$H$_{52}$), then the reactor may operate in temperature ranges of approximately 300° F. to 500° F. and preferably about 400° F., while the pressure in the reactor is maintained in a range of about 100 psig to 500 psig and preferably about 400 psig. Example reactant flow rates would include about 75 to about 1000 standard cubic centimeters per minute (SCCM) for CO and about 150 to about 2000 SCCM for H$_2$. The ratios ranged from 1.0 to 2.0 H$_2$/CO.

In an alternate Fischer-Tropsch process embodiment, the reactor comprises substrate elements having elongated micro-structures of at least one of cobalt, iron, or ruthenium. The carbon compound and hydrogen are fed into the reactor and reacted with the catalyst at a temperature (i.e., the average internal temperature of the reactor) between about 80° F. and about 200° F. (or any sub-range therebetween). In another variation of this embodiment, the carbon compound and hydrogen are reacted with the catalyst at a temperature between about 90° F. and about 150° F. In any of the FTP embodiments described herein, the carbon compound (e.g., carbon monoxide) and hydrogen may be supplied at a mass ratio ranging from about 1:1 to about 1:3 and more preferably about 1:1 to about 1:2. Generally the reactor temperature will vary with pressure. At lower temperatures, the reactor pressure may be between about 0 and 5 psig. More commonly the reactor pressure may be between about 5 and 50 psig (or any sub-range therebetween). However, other embodiments may run at a reactor pressure of between about 0 and 400 psig (or any sub-range therebetween).

In another alternate embodiment, the reactor may be a conventional plate frame heat exchanger. In this type of heat exchanger, there are typically two alternating chambers or pathways, usually thin in depth, separated at their largest surface by a corrugated metal plate. The plates may be spaced by sealing gaskets which are placed into a section around the edge of the plates. In an alternate embodiment the plates are welded together and no gaskets are required. The plates are often pressed to form troughs at right angles to the direction of flow of the liquid which runs through the channels in the heat exchanger. These troughs are arranged so that they interlink with the other plates which forms the channel with narrow gaps on the order of millimeters (e.g., 1.3-1.5 mm) between the plates.

The catalyst micro-needles will be formed on the plate surfaces of the pathway which is exposed to the reactants. A temperature control (typically cooling, but also heating in other embodiments) fluid circulates through the other pathway. In a modification of this embodiment, the reactant(s) may be mixed in a diluent. For example, where CO and H$_2$ are the reactants, these reactants could be mixed decane or hexane as diluents prior to entering the reactor.

Figure 10A:
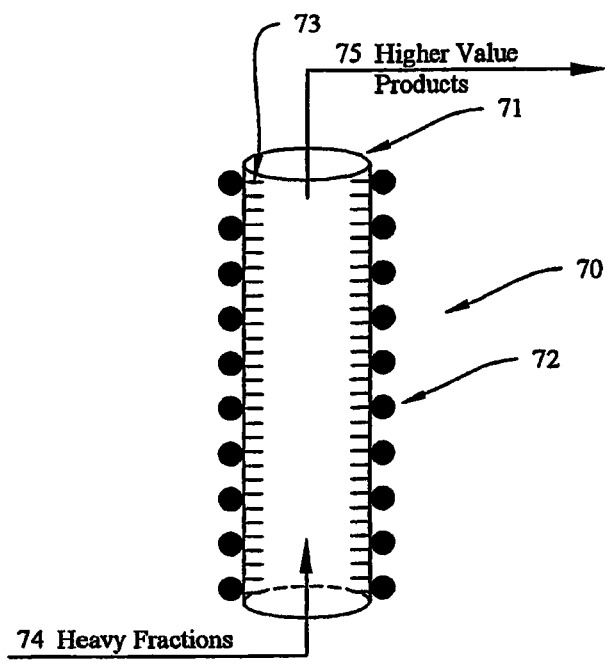
FIGS. 10A and 10B schematically illustrate petroleum cracking and reforming processes.

A further embodiment seen in FIG. 10A is a reactor column 70 which generally comprises a riser tube 71 with a temperature control coils 72 contacting the outside of riser tube 71 and micro-structures 73 formed either directly on the inside surface of riser tube 71 or on separate substrate elements positioned in the riser tube 71. Reactants will enter via input path 74, contact the catalyst structures 73 and product(s) exit via exit path 75. In one example, reactor column 70 may be used in a fluid catalytic cracking process, where preheated high-boiling petroleum feedstock (at about 315 to 430° C.) consisting of long-chain hydrocarbon molecules is injected into the catalyst riser where it is vaporized and cracked into smaller molecules of vapor by contact with the catalyst micro-structures. In such embodiments, the catalyst may be platinum or iron coated with platinum.

Figure 10B:
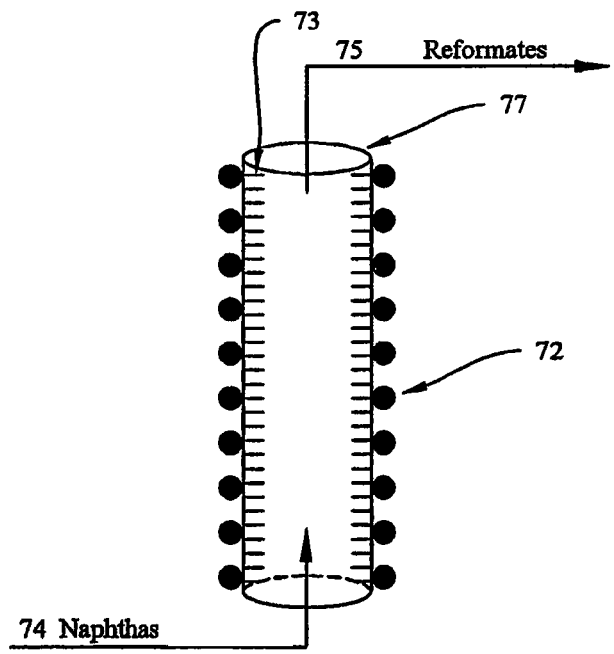

Alternatively, the reactor column 77 in FIG. 10B could be employed in petroleum reforming process which converts petroleum refinery naphthas, typically having low octane ratings, into high-octane liquid products which are components of high-octane gasoline. The liquid feed is joined by a stream of hydrogen-rich gas and the resulting liquid-gas mixture is preheated by flowing through a heat exchanger. The preheated feed mixture is then totally vaporized and heated to the reaction temperature (495 to 520° C.) before the vaporized reactants enter the reactor. Although FIGS. 10A and 10B schematically illustrate catalyst micro-structures 73 on the sides of the reactor columns, it will be understood that the catalyst could be positioned on any substrate structure located anywhere in within the column.

Figure 11:
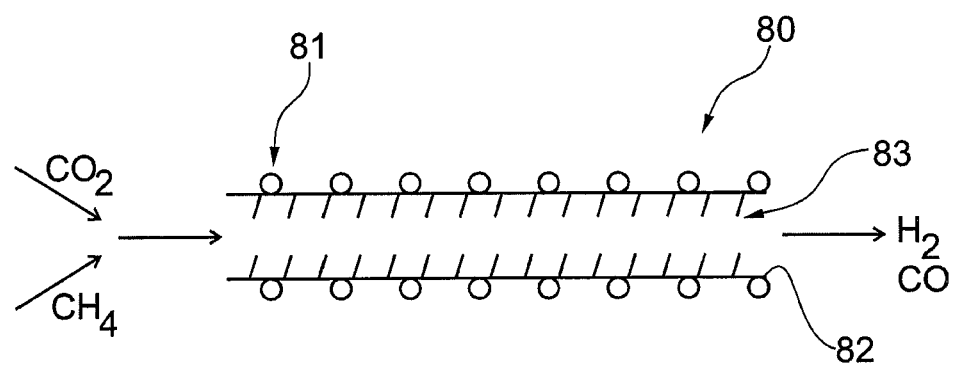
FIG. 11 schematically illustrates a dry reforming process.

Another embodiment suggested in FIG. 11 involves dry reforming of methane to produce syngas. This reactor 80 includes a temperature control mechanism 81. Reactor 80 could be any conventional reactor such as the plate frame reactor or one of the tubular reactors described above. Temperature control mechanism 81 could be heating/cooling coils, fluid exchange conduits, or any other conventional temperature control methods. A substrate surface 82 within reactor 80 will include catalyst microneedles 83. In a dry methane reforming embodiment, the catalyst would be nickel microneedles, e.g., solid nickel structures or structures coated with nickel. The inputs or reactants in this embodiment will be $CO_2$ and $CH_4$ while the output products would be predominately $H_2$ and CO and unconverted CO2 and CH4.

Figure 12:
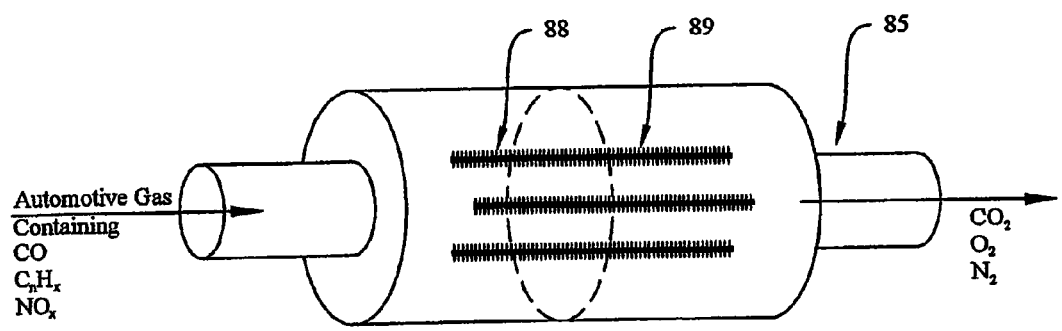
FIG. 12 schematically illustrates a catalytic converter system.

FIG. 12 illustrates a reactor type which could serve as a catalytic converter in an automobile exhaust system. Catalytic converter 85 may generally comprise a reactor body containing a catalyst substrate and catalyst microneedles formed on the substrate. In one embodiment, the substrate elements comprise a plurality of rods positioned parallel to the flow path of the reactor body. Typically, the input reactants will be automotive exhaust gases such as CO, $C_nH_y$, and $NO_x$ and the outputs are $CO_2$, $O_2$, and $N_2$. Certain embodiments may contain only one catalyst type in the reactor. In other embodiments, the reactor may have a first set of substrate elements 88 with microneedles formed of a reduction catalyst and a second set of substrate elements 89 with of microneedles formed of an oxidation catalyst. Non-limiting examples of reduction catalyst include platinum and/or rhodium and oxidation catalyst include platinum and/or palladium.

Figure 13:
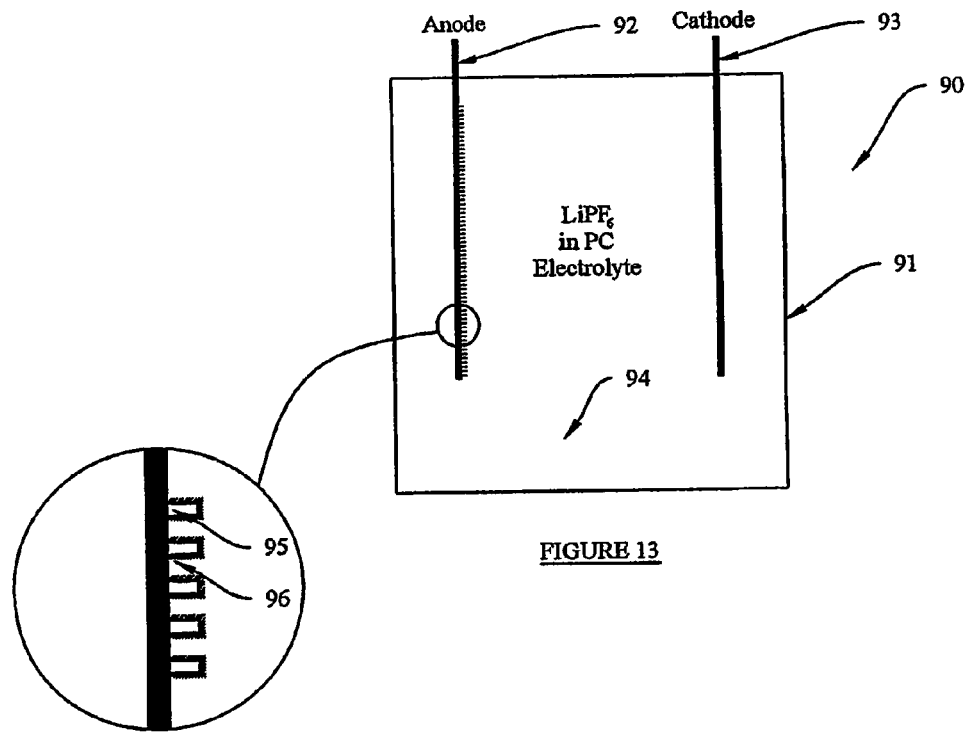
FIG. 13 schematically illustrates a lithium-ion cathode embodiment.

FIG. 13 illustrates an embodiment wherein the microneedles form part of an lithium-ion anode. The lithium-ion battery 90 includes battery body 91 having an anode 92, a cathode 93, and electrolyte 94. The cathode is generally one of three metal oxide materials: a layered oxide (such as lithium cobalt oxide), one based on a polyanion (such as lithium iron phosphate), or a spinel (such as lithium manganese oxide). The electrolyte is normally a lithium salt in an organic solvent. One typical example is a mixture of organic carbonates such as ethylene carbonate or diethyl carbonate containing complexes of lithium ions. These non-aqueous electrolytes generally use non-coordinating anion salts such as LiPF6, LiAsF6, LiClO4, LiBF4 and lithium triflate. One embodiment of the anode 92 is conductive metal having micro-needles 95 formed thereon with a carbon layer 96 subsequently formed on the micro-needles 95. In one preferred embodiment micro-needles 96 are copper. One example method of applying a carbon layer to the micro-needles is using a plasma enhanced chemical vapor deposition technique to produce a harder, more diamond-like carbon layer. Another example uses a low pressure chemical vapor deposition technique to produce a less hard graphite-like carbon layer.

Figure 14:
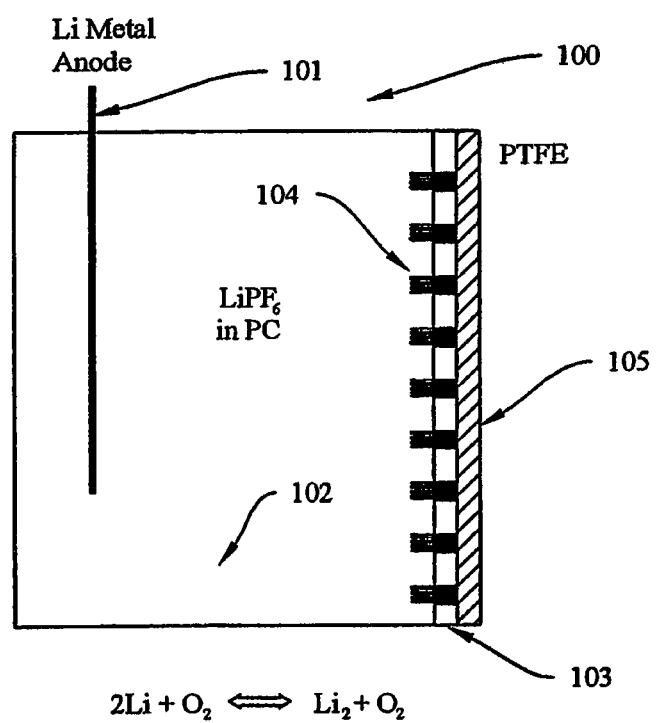
FIG. 14 schematically illustrates a lithium-air cathode embodiment.

FIG. 14 illustrates an embodiment wherein battery 100 comprises Li metal anode 101 in $LiPF_6$ electrolyte 102. The cathode is formed of a perforated metallic membrane 103 with a PTFE membrane 105 which allows $O_2$ to escape the battery but prevents the migration of moisture ($H_2O$) from contacting the battery electrolyte. In preferred embodiments, perforated metallic membrane 103 is a then plate of either Co, Au, or Ni with 10 um to 1 mm pores formed thereon. In these embodiments, Co is one possible catalyst for micro-needles 104. During discharge, lithium cations flow from anode 101 through an electrolyte 102 and combine with oxygen at the cathode to form lithium oxide $Li_2O$ or lithium peroxide $Li_2O_2$; thereby inducing the flow of electrons from the battery's anode to the cathode through a load circuit. The micro-needles catalyze the combining of $Li_2$ and $O_2$ during discharge and catalyze the disassociation of these molecules during charging.

Figure 15:
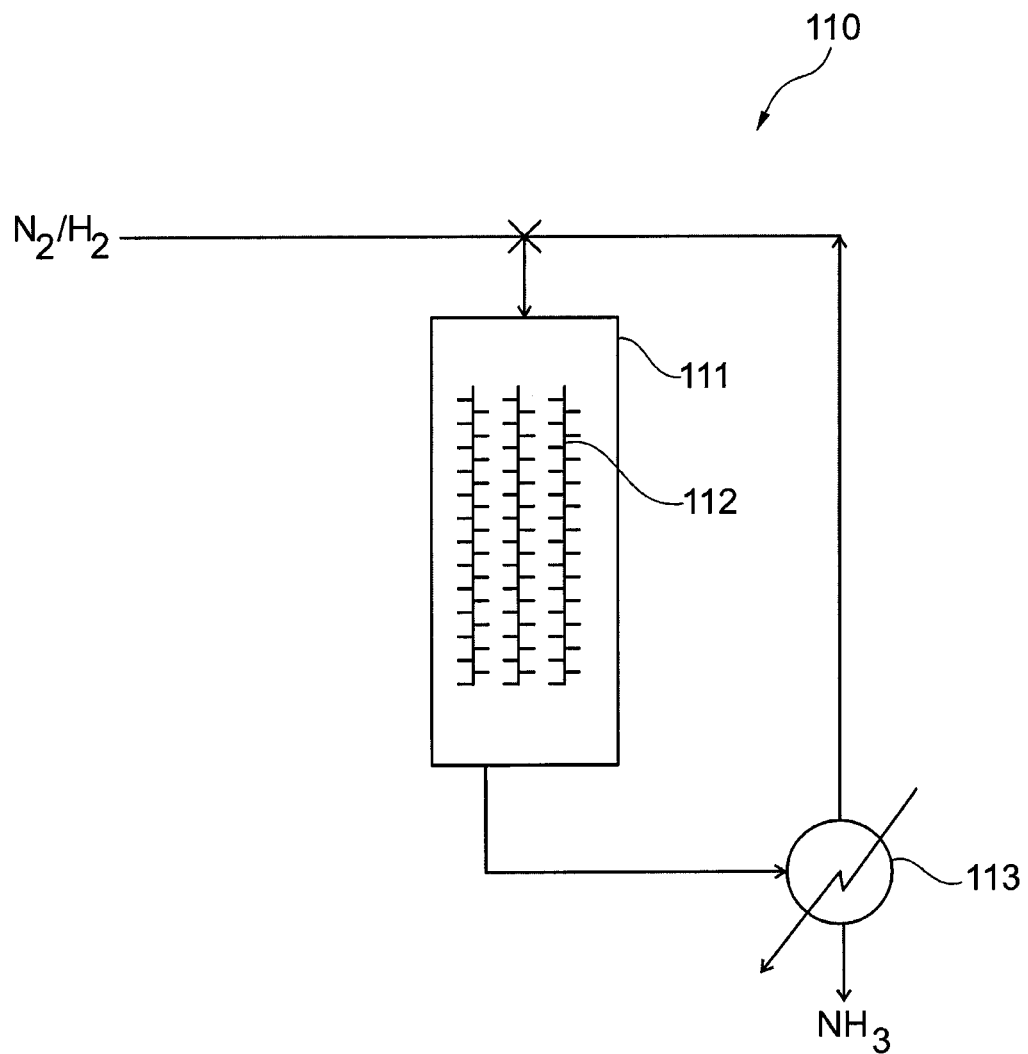
FIG. 15 schematically illustrates a Haber-Bosch process embodiment.

FIG. 15 illustrates a reactor 111 that could be employed in a Haber-Bosch process 110. Reactants N2 and H2 are fed into high pressure reactor body 111 where the reactants contact micro-structure catalyst formed on substrate elements 112. In one embodiment, the N2 source is simply the surrounding atmosphere. The output containing ammonia and unreacted N2 and H2 are fed to cooler/condenser 113 which allows removal of ammonia and return of unreacted gases back the input of reactor body 111. In this example of the Haber-Bosch process, the catalyst micro-structures are formed of iron or alternatively iron with osmium tips or layers. Example pressure ranges within reactor 111 may be about 0 psig to about 1000 psig (or any sub-range therebetween).

Figure 16:
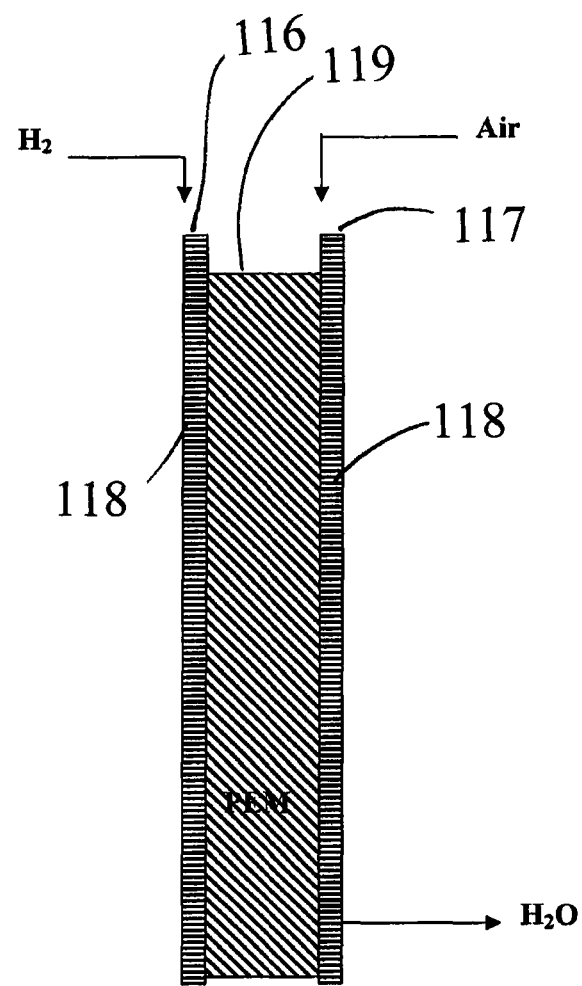
FIG. 16 schematically illustrates a fuel cell embodiment.

A still further embodiment in FIG. 16 schematically represents fuel cell 115. Fuel cell 115 generally comprises hydrogen diffusion plate 116 and oxidant diffusion plate 117 with proton exchange membrane 119 positioned in between. Both diffusion plates 116 and 117 will have micro-needle catalyst structures 118 positioned therein. In FIG. 16, the catalyst metal from which the micro-needles are formed is preferably platinum. Within hydrogen diffusion plate 116 the catalyst micro-needles catalyze the disassociation of protons from the hydrogen and in oxidant diffusion plate 117 the combination of $O_2$ with hydrogen to form water.

Figure 17:
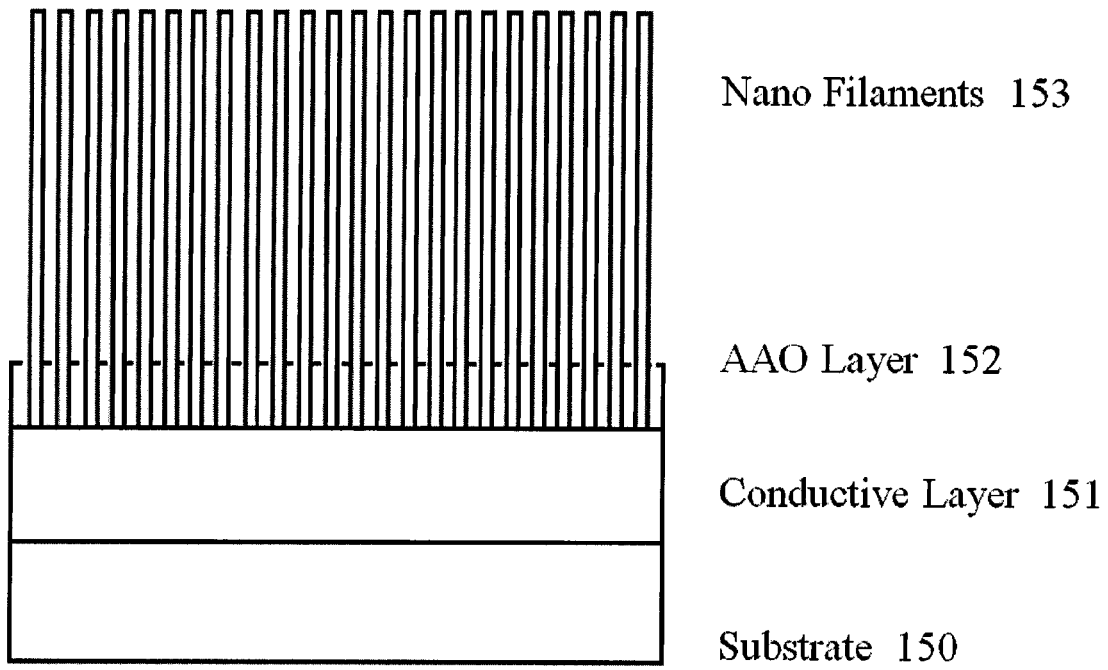
FIG. 17 illustrates another alternate method of forming the catalyst micro-structures on a substrate.

Another method of forming the catalyst micro-structures is suggested by FIG. 17. In this embodiment, the catalyst microneedles or micro-filaments are formed in a process that generally includes the step of forming an anodized aluminum oxide (AAO) layer on the substrate layer. The embodiment of FIG. 17 illustrates a substrate 150, a conduction layer 151, an AAO layer 152, and catalyst filaments 153 formed through the AAO layer 152 and extending beyond the AAO layer 152. In the particular embodiment of FIG. 17, the substrate is formed of a nonconductive material. Nonlimiting examples of such nonconductive materials include, ceramics, polymers, and oxide coating on a conducting substrate, and concrete. The nonconductive material may also include semiconductive materials such as silicon or silicon based compounds. In many embodiments, the non-conductive material will have a resistivity of greater than about 0.15 ohm-cm. As described above, in many embodiments, the substrate material 150 will be substantially nonporous.

In FIG. 17, a conduction layer 151 is shown formed on substrate 150. This embodiment of conduction layer 151 is typically formed of a generally conductive material, commonly having an electrical conductivity of at least 1,000,000 $\Omega^{-1} \cdot m^{-1}$, and more particularly in the range of metals such as copper (59,170,000 $\Omega^{-1} \cdot m^{-1}$), aluminum (37,450,000 $\Omega^{-1} \cdot m^{-1}$), titanium (1,852,000 $\Omega^{-1} \cdot m^{-1}$), or chromium (8,000,000 $\Omega^{-1} \cdot m^{-1}$). In preferred embodiments, the conduction layer 151 is formed of a material which is capable of withstanding the anodizing environment and the process conditions under which the catalyst will ultimately be used. Non-limiting examples of materials suitable for forming the conduction layer 151 include titanium and chromium and alloys thereof. The conduction layer 151 typically needs only have a sufficient thickness or depth to form a conductive base for the forming of further metal layers on the conduction layer 151. For example, in many embodiments, conduction layer 151 will be at least 5 nm thick and more preferably at least 20 nm thick. Likewise in these embodiments, it may be preferred that the conduction layer 151 be less than 200 nm thick and more preferably less than 100 nm thick. Conduction layer 151 may be formed on substrate 150 by any conventional or future developed process, including chemical vapor deposition, thermal or electron beam evaporation, or sputtering.

Once the conduction layer 151 has been deposited on the substrate, a film of aluminum is formed on the conduction layer 151 which ultimately is anodized to form the AAO layer 152. In more general embodiments, the aluminum film will range from about 300 nm to about 2000 nm in depth, but could be any sub-range there between. In more preferred embodiments, the aluminum film will range between about 600 nm and about 800 nm. Again, the aluminum film may be formed on conduction layer 151 by any conventional or future developed process, including chemical vapor deposition, thermal or electron beam evaporation, and sputtering, although preferred deposition processes include thermal evaporation or electron beam evaporation.

In situations where the substrate 150 is itself formed of a sufficiently conductive material, the conduction layer 151 may not be necessary and the aluminum may be formed directly on the substrate. Example of sufficiently conductive substrate materials include stainless steel, titanium, nickel, and chromium. Nevertheless, even when working with a conductive substrate, certain preferred embodiments will first form a non-conductive layer (e.g., ceramic layer or AAO layer) between the conductive substrate 150 and the conductive layer 151.

After the aluminum film is formed on conduction layer 151 (or directly on a conductive substrate), it will be anodized to form the AAO layer 152. The reaction between aluminum and oxygen reduces the density of the aluminum layer, causing the AAO layer to be thicker than the original aluminum layer. In certain experiments, it was found that the AAO layer was about 40% thicker than the original aluminum layer. As suggested above, the anodizing process will convert the aluminum layer into AAO layer 152 and form pores in the AAO layer, with electrolyte concentration, acidity, solution temperature, and voltage being controlled to allow the formation of a consistent oxide layer and also to control the size and density of the pores. In certain preferred embodiments, the anodizing process will be controlled to produce an AAO layer having pores ranging from about 10 nm to about 500 nm (or any subrange therebetween) and more preferably between about 10 nm and about 200 nm. In certain embodiments, the anodizing process is carried out until substantially all aluminum oxide within the pores is removed and the pores expose the underlying layer. Similar to above embodiments, the pore density (i.e., the sum of cross-sectional area of the pores divided by the substrate surface area over which the pores are distributed) may range anywhere from about 10% to about 95%. However, in more preferred embodiments, the pore density will be at least about 35%, and more preferably at least about 40%, 50%, 60%, 70%, 80%, 90%, or 95%.

While many different anodizing conditions could be employed to produce the above pore size and density, one preferred anodizing technique, where the substrate was silicon with a titanium conduction layer, is anodizing with a 2% sulfuric acid solution at 0° C. in a two-step process. The first anodizing step is carried out for about six minutes and the second anodizing step carried out for about 20 minutes. Both steps are conducted at 18V. A 3% phosphoric acid etch procedure may be carried out between the anodizing steps in order to remove the AAO layer formed during the first anodizing step. In certain embodiments, after the first anodization, the AAO is removed from the aluminum by a wet etching solution that has a high etch rate of AAO and a low etch rate of aluminum. This leaves behind a semi-regular pattern of scallops. Then a second anodization is performed on this semi-regular pattern which assists the pattern to become more regular.

One preferred anodizing technique, where the substrate was silicon with a titanium conduction layer, is anodizing with a 2% sulfuric acid solution at 20° C. in a three-step process. The first anodizing step is conducted at 12 volts with the substrate serving as the anode and with another aluminum conductor serving as the cathode. This process is continued until there is a sharp drop in current. Typically the final current is approximately less than 100 micro amps per $cm^2$. At this point, a second phase of the process is conducted in which the polarity of the electrodes is reversed, where the substrate becomes the cathode and the aluminum electrodes that had served as the cathodes become the anodes. The potential in this region is approximately 3.5 volts. This phase typically lasts less than one minute. The third phase reduces the applied potential to 2.5 volts and typically lasts approximately 1 minute.

In certain preferred embodiments. the aluminum layer is subject to the anodizing process until at least about 80%, or more preferably at least about 90%, or most preferably at least about 95% by weight of the aluminum layer is converted to the aluminum oxide (AAO) layer.

Once the anodizing process is complete, the substrate will have a series of catalyst material micro/nano-needles or filaments formed thereon. In many embodiments, the filaments will be formed by an electroplating process where the filaments begin accumulating in the pores in the AAO layer until the filaments generally have a length of between about 30 nm to about 5000 nm (or any subrange therebetween) beyond the AAO layer. In one preferred embodiment, the lengths of the filaments will be between about 500 nm and about 2500 nm. While various conventional and future developed electroplating processes may be used, one preferred process is pulse reverse electroplating, wherein the process includes cathodic pulses and anodic pulses, often with rest periods between the pulses. As one nonlimiting example, the plating program consists of an 8 to 10 ms cathotic pulse, a 2 ms anodic pulse, and a 500 to 600 ms rest period. The cathotic pulse is controlled with a current density of 50 $mA/cm^2$ and a compliance voltage of 10V. The anodic pulse is controlled at a potential of 3V and a compliance current density of 50 $mA/cm^2$. This process is continued until the filaments have reached the desired length, e.g., 3 hrs to electroplate filaments approximately 2000 nm in length. Other examples may include processes where the pulse reverse electroplating includes a current density of about 1 $mA/cm^2$ to 200 $mA/cm^2$, a forward (cathotic) pulse time of about 1 ms to 500 ms, a reverse (anodic) pulse time of about 1 ms to 500 ms, and a rest period of about 10 ms to 2,000 ms. Alternatively, the pulse reverse electroplating includes a current density of about 50 $mA/cm^2$ to 75 $mA/cm^2$, a forward (cathotic) pulse time of about 4 ms to 120 ms, a reverse (anodic) pulse time of about 1 ms to 30 ms, and a rest period of about 10 ms to 2,000 ms.

In certain embodiments, any remaining aluminum oxide from the initial AAO layer is removed during or after the electroplating process, but such removal of remaining aluminum oxide is considered optional in most embodiments.

One characteristic of the filaments produced through this process is the filaments tend to have a degree of twisting which enhances catalytic activity by providing more active sites. One example includes the filaments having radius of curvatures (in any direction) from the vertical centerline (or any other direction of filament growth) of 15 nm to 10 um. Another characteristic is that the overall filament array will have a "packing density" or a given total mass of filaments per unit of surface area over which filaments are formed. In certain embodiments, the packing density will be between at least about 5 mg/cm$^2$ and about 200 mg/cm$^2$. However, the packing density can also be at least any amount between 5 mg/cm$^2$ and about 200 mg/cm$^2$ (e.g., 20 mg/cm$^2$, 50 mg/cm$^2$, 100 mg/cm$^2$, 150 mg/cm$^2$, etc.), or even outside the range of 5 mg/cm$^2$ and about 200 mg/cm$^2$.

Although particular embodiments of the filaments may have lengths greater than 5000 nm, excessively long filaments may tend to coalesce, thereby reducing the number of catalytically active sites per gram of catalyst material. For example, it is believed that excessively long filaments causes a reduction in the porosity at the upper end of the filament array. In certain instances, the excessive lengths of the filaments cause the upper ⅓ of the filament array to become less than 10% porous by volume (or alternatively less than 5% porous, 3% porous, or 1% porous).

The filaments may be formed of any catalytic material. Preferred examples include cobalt, iron, ruthenium, nickel, platinum, palladium, rhodium, osmium, vanadium, copper, aluminum, other transition elements, lanthanides, actinides, and fourth, fifth, and sixth period elements. The filaments could be formed completely of one element, could be a non-catalyst material coated with a catalyst layer, or could include filaments formed from a first catalyst material (e.g., cobalt) and capped with a section of a second catalyst material (e.g., ruthenium). The catalyst materials could also be alloys whose compositions include cobalt, iron, or ruthenium together with another elements or compounds. The nanowires may consist on alternating layers of different catalyst materials Substrates having the catalyst filaments described above may be used in any number of catalytic processes. A Fischer-Tropsch process is one example wherein substrate elements are positioned in a reactor and a carbon compound (as described above) and hydrogen are injected into the reactor such that at least a portion of the carbon compound and hydrogen contact the catalyst filaments (cobalt in this example). The reactant flow rates provided above form one appropriate example, but naturally those skilled in the art will recognize many alternative reactant flow rates. The carbon compound and hydrogen are then reacted with the catalyst filaments at a temperature of between about 100° F. and about 500° F. and a pressure of less than about 500 psig. Alternatively, the temperatures could be any sub-range between about 100° F. and about 500° F., e.g., about 150° F. and about 400° F. and the pressure could be less than 500 psig, e.g., under 400 psig, 350 psig, 300 psig, 250 psig, 200 psig, 150 psig, 100 psig, or 50 psig. More preferably, the temperature may be between about 150° F. and about 300° F. and a pressure of less than about 200 psig.

The catalyst filaments described above may be utilized in other catalyst based reactions. For example, a Haber-Bosch process may be carried out utilizing iron catalyst filaments and H2, N2 reactants (i.e., contemplating the reaction N2+3H2>2NH3). Pressure and temperature in such a process would be under about 600° F., and under about 2500 psig, and more preferably under about 550° F., 500° F., 450° F., 400° F., 350° F., or 300° F. and under one of about 2000 psig, 1750 psig, 1500 psig, 1250 psig, 1000 psig, 800 psig, 700 psig, 600 psig, or 500 psig.

One alternative embodiment is a Fischer-Tropsch process reactor surface comprising (a) a substrate element having a surface; and (b) a plurality of elongated micro-structures of catalyst material attached to the substrate surface, the micro-structures comprising a width of less than about 1 um.

Another embodiment is a Fischer-Tropsch process reactor surface comprising (a) a substrate element having a surface; and (b) a plurality of elongated micro-structures of catalyst material attached to the substrate surface, the micro-structures comprising a crystal structure having substantially no grain boundaries.

A still further embodiment (Embodiment A), is a catalytic reactor comprising (a) an enclosed reactor body including at least one reactant entrance port and at least product exit port; (b) at least one substrate element including a surface and being positioned within the reactor body; and (c) a plurality of elongated micro-structures of catalyst material attached to the substrate surface, the micro-structures comprising a width of less than about 1 um and a length at least five times the width. Alternatives to Embodiment A could include (in the alternative): (i) a temperature control mechanism regulating process temperatures of the reactor; (ii) a pressure control mechanism regulating process pressures of the reactor; (iii) the catalyst being at least one of cobalt, iron, ruthenium, nickel, platinum, palladium, rhodium, or copper; (iv) the micro-structures comprising a crystal structure having substantially no grain boundaries; (v) the micro-structures having a width of less than about 500 nm and a length at least ten times the width; (vi) the temperature control mechanism comprising a cooling conduit which forms part of the substrate or upon which the substrate is positioned: (vii) the substrate element consisting substantially of a metal or a metal coated material; (viii) the substrate element being a plate member or a tubular member; (ix) the substrate element comprising a plurality of plates positioned in series in a flow path of the reactor body; (x) a first plurality of micro-structures comprising a reduction catalyst and a second plurality of micro-structures comprising an oxidation catalyst; (xi) the reduction catalyst comprising platinum and/or rhodium and the oxidation catalyst comprises platinum and/or palladium; (xii) the substrate element being substantially nonporous; (xiii) temperature control elements being in contact with the reactor body; (xiv) the reactor body forming a catalyst riser in a fluid catalytic cracking process; (xv) the micro-structures of catalyst material comprising iron coated with platinum; (xvi) napthes being the reactant inputs; (xvii) the catalyst material comprising at least one of nickel, platinum, cobalt, or iron.

Another embodiment is a catalyst reaction process comprising the steps of: (a) providing a reactor comprising a substrate element having a surface and a plurality of elongated micro-structures of catalyst material attached to the substrate surface, the micro-structures comprising: (i) a width of less than about 1 um; and (ii) a length at least five times the width; (b) injecting at least two reactants into the reactor such that at least a portion of the reactants contact the catalyst material; and (c) reacting the reactants with the catalyst at above ambient pressure. This embodiment could also include the alternative wherein the reactants are reacted with the catalyst at a temperature of less than about 200° F. and a pressure of less than about 50 psig.

EXPERIMENTAL EXAMPLES

Example I

Figure 6:
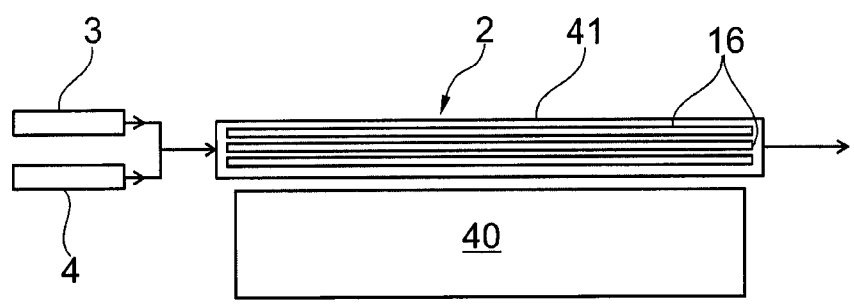
FIG. 6 schematically illustrates the reactor system utilized in one experimental example.

A reactor 2 (shown schematically in FIG. 6) was fabricated from one inch OD autoclave tubing and was six inches in length. The catalyst substrates were three ¼ inch diameter aluminum rods approximately two inches in length. The rods 16 were allowed to rest on one another with no specific structure spacing the rods 16 apart. The reactor 2 was sealed on each end with standard "Swagelok®" compression fittings.

Micro-catalyst needles were formed on the substrate rods 16 with the following process. First, the substrates 16 were mechanically cleaned. Using household cleaners (e.g., Lysol or Formula 409), the substrates 16 were presoaked in the cleaner for approximately 20 minutes. Using a wire brush or other abrasive cleaners, the substrates 16 were scrubbed to remove any mill scale or dirt. The substrates 16 were then returned to the cleaning bath for 20 minutes. Second, a commercially available alkaline cleaner was heated to 140° F. and the substrates 16 were immersed in the solution for 20-30 minutes. Third, the aluminum substrates 16 were chemically etched using a weak solution of sodium hydroxide. This solution was maintained at approximately 110° F. The substrates 16 were submerged in the solution for 20 seconds to one minute. If the substrates 16 foamed excessively, they were removed from the solution. Fourth, the substrates 16 were deoxidized. Surface etching typically leaves behind some oxidized material or smut. This material should be removed before anodizing. Commercial aluminum desmutting solutions are recommended to accomplish this task. This example process used a commercial "Desmut AL-1" at a concentration of 9 ounces per gallon of solution. Immersion times vary due to the degree of oxidation, but generally were in the range of one to three minutes. Fifth, substrate anodization was conducted in a sulfuric acid solution at a concentration of 8 ounces per gallon of solution. The solution was not heated, but was agitated. The substrates 16 to be micro-templated were connected to the anode terminal of a DC power supply and immersed in the acid solution. A cathode from the power supply was also immersed in the solution. Substrates 16 were anodized with a current density of about 0.1 A/in$^2$. DC potential typically ranged from 10 to 20 volts. Typically, a 20 minute anodizing process was used to produce the nanostructured template having micropores on the order of 10 nm.

Lastly, the catalyst micro-needles were formed on the substrate 16. For purposes of this example, cobalt was selected as the catalyst material to be plated. The source of cobalt used was cobalt nitrate and a solution of two ounces $CoNO_3$ per gallon of solution was prepared. The substrates 16 to be plated were immersed in the solution and connected to a cathode of a DC power supply. The anode for the power supply was connected to another electrode and also immersed in the $CoNO_3$. A current density of 0.050 A/in$^2$ with a DC potential of two to three volts. This process was continued for 2 to 8 hours to produce micro-needles about 10 nm in diameter and 5 um in length with a packing density of about 30%.

Figure 8:
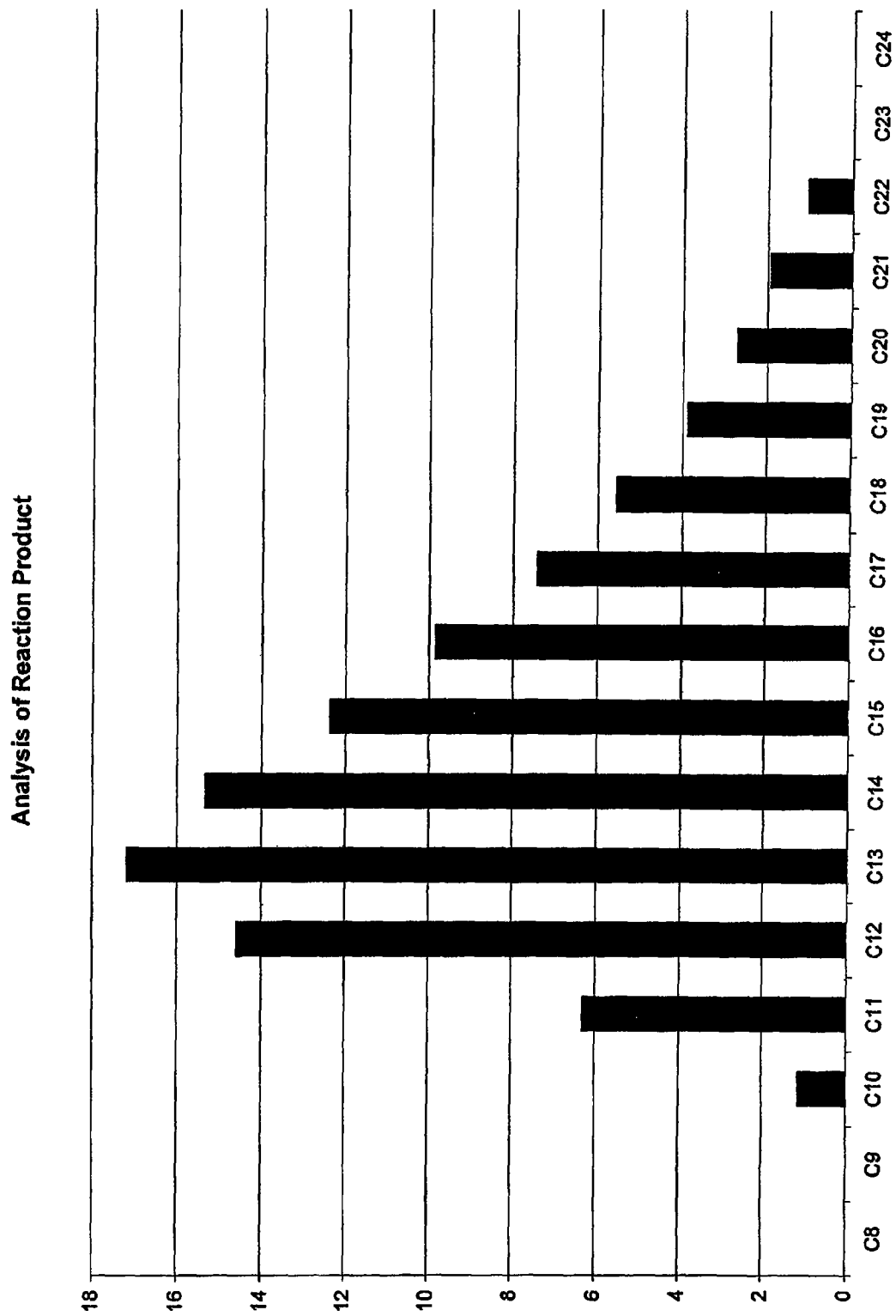
FIG. 8 illustrates the hydrocarbon distribution from an experimental example.

The reactor tube 41 (with substrate rods 16 inserted) was placed on a hot plate 40 and connected to a source of reactant gases at one end of the tube and the opposite end of the tube was connected to a flask and products were collected at atmospheric temperature. Reaction gases were obtained from cylinders provided by Nexaire® Gasses and were regulated to approximately 450 PSIG and gas flow was controlled with "Aalborg" mass flow controllers. The reactor 2 pressure was maintained by a back pressure regulating valve obtained from "Swagelok". The hot plate 40 was kept at about 400° F. After the catalyst was loaded, the reactor 2 was purged to remove contaminants and then pressurized to 400 psig. A flow of hydrogen was established and the temperature was increased to approximately 400° F. Carbon monoxide and hydrogen were introduced into the reactor 2 at stoichiometric ratios and a reactor space velocity of 0.14 min$^{-1}$ was achieved. Reaction gases flowed into the reactor 2 reacted on the surface of the catalyst and the products exited the reaction space at high temperature (~400° F.) and high pressure (~400 PSIG) in one phase. The reactor 2 was continuously operated in the above described regime for 13 days. There was cooling of the product when it exited the reactor 2 through the back pressure regulator and product collection was at atmospheric temperature. After the pressure was reduced in the backpressure regulator, the reaction products were cooled and the liquid/solid phases produced were collected. The denser phases were separated from the gasses in a single stage as the reaction products were collected. No evidence of charring or coking of the catalyst micro-needles was seen. Analysis showed the CO conversion was approximately 0.045 mol CO/mol Co—min. FIG. 8 shows the hydrocarbons produced and their percentage distribution.

Example II

Figure 7:
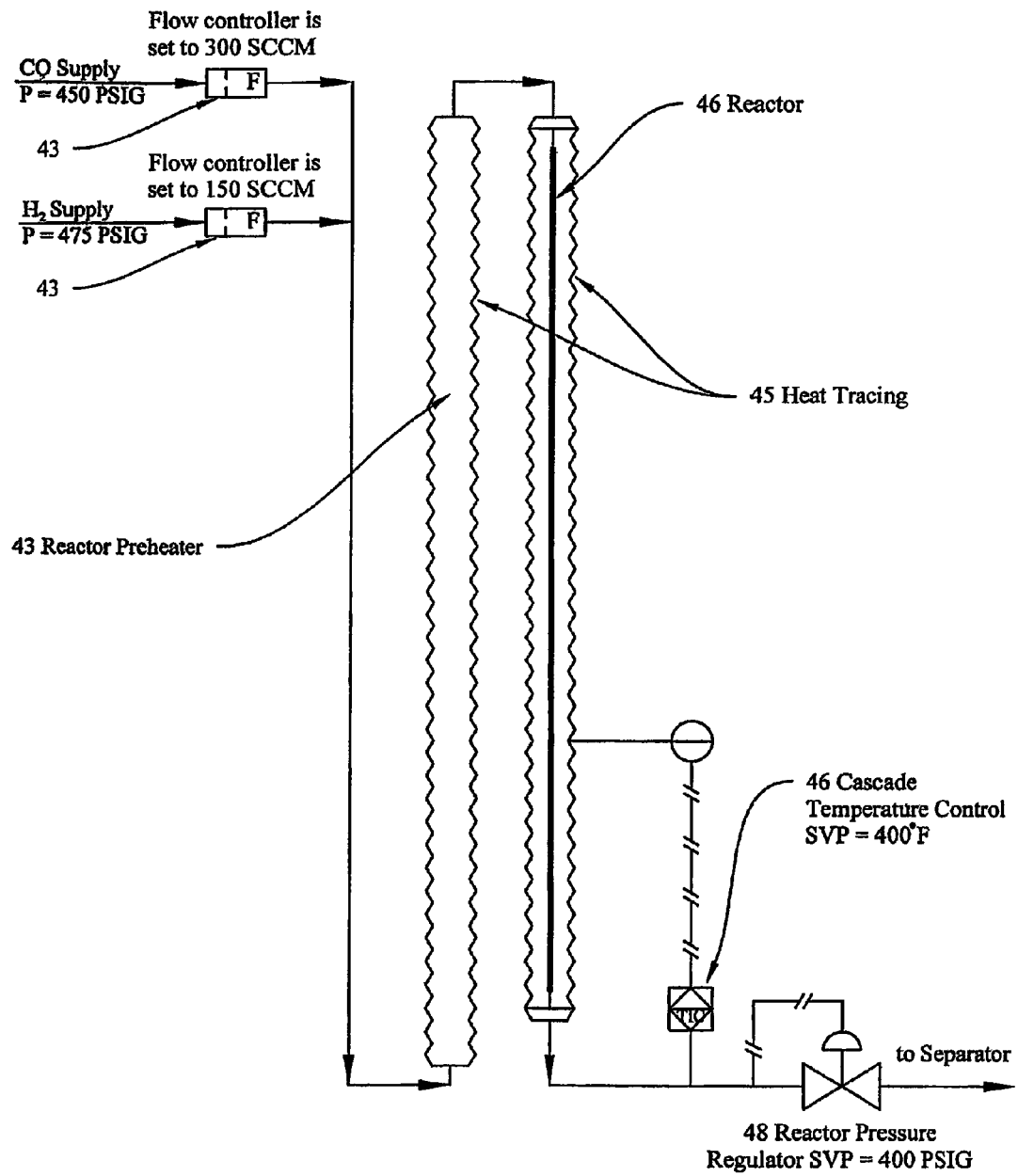
FIG. 7 schematically illustrates the reactor system utilized in another experimental example.

Another reactor was fabricated from one-half inch autoclave stainless steel tubing and was about eighteen inches long as suggested in FIG. 7. CO and $H_2$ reactants were supplied from cylinders and controlled at 450 PSIG. Reactant flowrates were controlled by Aalborg® mass flow controllers 43. The reactants first passed through a preheater 44 constructed of ¼ inch stainless steel tubing about 18 inches in length with heating trace 45 wrapped around the tubing. The reactor tube likewise was wrapped with heating trace 45. The reactor system also included a cascade temperature controller 46 and a Swagelok back-pressure regulator 48. Although not shown in FIG. 7, the reactor system included a separator which received the reacted product and removed water from the hydrocarbons. A simple separator was formed with a five gallon glass carboy that separated the liquid products from the vapor products. The catalyst substrates were ¼ inch aluminum 6061-T6 all thread rods with cobalt micro-needles formed as described in Example I.

After four rods were inserted into the reactor and supported in the vertical position by the rod threads engaging compression fittings at the reactor exit end, the other reactor end was sealed using "Swagelok" compression fittings. The flow controllers were set at 300 SCCM for CO and 150 SCCM for $H_2$. The reactor temperature was controlled at 400° F. with the heating traces 45 and the pressure was regulated at 400 PSIG using the back-pressure regulator 48. The temperature of the exiting fluid was measured using a thermowell and a "J" type thermocouple. This temperature was controlled by manipulating the reactor wall temperature (by cycling the heat tracing on/off) which was measured by a surface thermocouple in a cascade mode. The product produced was a hydrocarbon mixture which consisted substantially of C—numbers that are normally considered in the diesel range.

Example III

Figure 9:
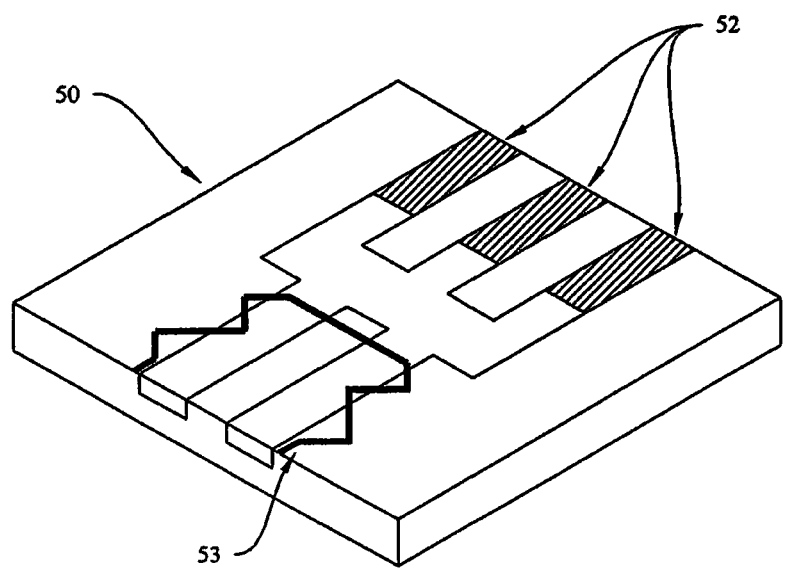
FIG. 9 illustrates a test reactor device for another experimental example.

As suggested by FIG. 9, a multi-channel borosilicate microreactor 50 was fabricated in order to conduct simultaneous testing of various forms of cobalt catalysts. The top piece of the microreactor had channels 52 etched via a polymer mask and sandblasting. The bottom piece of the microreactor had a restive heater 53. See Brown, et al., Microreactors for Synthetic Diesel Production to Optimize Nanostructured Cobalt Catalyst, Institute for Micromanufacturing, LA Tech University, 2009, which is incorporated by reference herein in its entirety.

Fabrication of the metal (e.g., Al) strips was performed via deposition, photolithography, and etching steps. Photoresist S1813 was used for the photolithography portion of the fabrication. Process steps included a 3000 rpm, 1 min photoresist spin, 115° C., 2 min anneal, and 90 sec of UV exposure. The exposed Al from this process was etched with a solution of 1 vol % $HNO_3$ (Sigma Aldrich, 70%, A.C.S. reagent), 10 vol % $H_3PO_4$ (Alfa Aesar, 85% aq. soln.) with the remainder water and heated to 50° C. The undeveloped photoresist was removed with acetone.

A reference catalyst of cobalt was electroplated on one of the aluminum strips. The plating solution consisted of a 100 g/L aqueous solution of $CoCl_2.6H_2O$ and was plated at a current density of 30 mA/cm2 at room temperature for 2 min using a cobalt counter-electrode.

A second test catalyst of cobalt was impregnated into the pores of $Al_2O_3$ (alumina). The alumina was fabricated via anodization in oxalic acid followed by chromic acid etching. The anodization process typically produces small pores with increasing diameter as the alumina increases in thickness due to a steady drop of current density with constant voltage. Therefore the process was modified by maintaining a constant current density with a steadily increasing voltage yielding a cylindrical shape rather than a conical shape. A high current density was used to increase the interpore spacing followed by etching in chromic acid to increase pore diameter to approximately 100 nm. $Co(NO_3)_2$ was used as the aqueous cobalt source because of its high solubility of 134 g/100 mL. The solution was deposited onto the porous aluminum oxide structure and allowed to dry, thus allowing the metallic cobalt precipitate to stick to the inside of the pores.

A third catalyst was a cobalt nanowire catalyst. The same anodization as performed in the second catalyst was performed to obtain the porous aluminum oxide layer. Cobalt nitrate was used as the aqueous solution as well. The solution consisted of 7.6 wt % cobalt nitrate at room temperature with a potential of 2 V. The cobalt was deposited under a high magnetic field produced by a neodymium-iron-boron (NIB) magnet with a BHmax of 50 MGOe. Once the cobalt nanowires extended beyond the aluminum oxide substrate the intrinsic magnetic field of the wires and the NIB magnet continue to the keep the nanowires growing along the same crystalline planes.

The resulting nanowires had a diameter similar to the pore size and tapering to a point at their maximum height on the order of 10 μm obtaining high-aspect ratio nanostructures determined by a Hitachi S4800 scanning electron microscope (SEM) with an Edax Genesis energy dispersive spectroscopy.

Hydrogen and carbon monoxide were flowed into the reactor at variable stoichiometric ratios and heated to a variety of operation conditions ranging from 150° C. and 300° C. and 300 psi to 450 psi. The cobalt catalysts tested were in fixed bed reactor configuration. The liquid product formed in the channel with the magnetically formed nanowires at 280° C. and 410 psi produced a liquid phase composed of 94% diesel.

The catalyst formed of nanowires ran for more than 300 hrs without showing major signs of wear which is much higher than typical cobalt catalysts that generally have a lifetime of no more than one hour. Oxidation is the primary reason cobalt catalysts deactivate and coking is secondary. Coking is when multiple carbon atoms come together to form graphite. The significantly longer run time is probably due to a high crystallinity of the nanowires so oxygen in the reactant stream cannot permeate into the cobalt structure via grain boundaries. The long run time is also evidence that the open structure of the cobalt nanowires does not allow for hydrocarbon accumulation as happens in a porous cobalt catalyst.

The invention claimed is:

1. A Haber-Bosch process comprising the steps of:
   (a) providing a reactor including substrate elements having catalyst filaments formed on the substrates elements, the catalyst filaments comprising (i) a diameter of about 10 nm to about 500 nm; (ii) a length of about 30 nm to about 5000 nm; (iii) a packing density of between 5 mg/cm2 and about 200 mg/cm2; and (iv) being formed of a metal including iron;
   (b) injecting a nitrogen compound and hydrogen into the reactor such that at least a portion of the nitrogen compound and hydrogen contact the catalyst filaments;
   (c) reacting the nitrogen compound and hydrogen with the catalyst filaments at a temperature of less than about 600° F. and a pressure of less than about 2000 psig.

2. The process according to claim 1, wherein the nitrogen compound is N2.

3. The process according to claim 1, wherein the catalyst filaments comprise either iron or iron with osmium layers.

4. The process according to claim 1, wherein the reaction pressure is less than about 1250 psig.

5. The process according to claim 1, wherein the reaction pressure is less than about 1000 psig and the reaction temperature is between about 250° F. and about 450° F.

6. The process according to claim 1, wherein the substrate elements are substantially nonporous.

7. The process according to claim 1, wherein the filaments packing density is at least about 20 mg/cm2.

8. The process according to claim 1, wherein the substrate elements are formed of a conductive material.

9. The process according to claim 1, wherein the substrate elements are a nonconductive material with a layer of conductive material applied thereto.

10. The process according to claim 1, wherein the catalyst filaments have a diameter between about 10 nm to about 200 nm.

* * * * *